United States Patent [19]

Enders et al.

[11] 4,053,620
[45] Oct. 11, 1977

[54] COMBATING FUNGI WITH 1-ARYL-5-ALKYLIDENE-2,4-DIOXO-IMIDAZOLIDINES

[75] Inventors: Edgar Enders, Cologne; Paul-Ernst Frohberger, Leverkusen, both of Germany

[73] Assignee: Bayer Aktiengesellschaft, Leverkusen, Germany

[21] Appl. No.: 668,547

[22] Filed: Mar. 19, 1976

[30] Foreign Application Priority Data

Apr. 5, 1975   Germany .............................. 2514992

[51] Int. Cl.$^2$ .............................................. A01N 9/22
[52] U.S. Cl. ........................... 424/273 R; 260/309.5; 548/310; 548/309; 548/312; 548/314
[58] Field of Search ...................... 424/273; 260/309.5

[56] References Cited

U.S. PATENT DOCUMENTS

| | | | |
|---|---|---|---|
| 3,846,441 | 11/1974 | Mine et al. .......................... | 260/309.5 |
| 3,960,883 | 6/1976 | Hubele .............................. | 260/309.5 |

*Primary Examiner*—Leonard Schenkman
*Attorney, Agent, or Firm*—Burgess, Dinklage & Sprung

[57] ABSTRACT

Fungicidal compositions containing, and methods of combating fungi, using 1-aryl-5-alkylidene-2,4-dioxo-imidazolidines of the formula

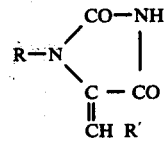
(I)

in which
R is aryl optionally substituted by nitro; by halogen; by alkyl, alkoxy, alkylthio, alkylsulfinyl or alkylsulfonyl each with up to 6 carbon atoms; by haloalkyl with up to 5 halogen atoms and 1 or 2 carbon atoms; by cycloalkyl with 5 or 6 carbon atoms; by hydroxyl; by cyano; by thiocyanato; by acetyl; by formyl; by phenyl or phenoxy each optionally carrying halogen or nitro as substituents; by phenylthio; by phenylsulfonyl; by halosulfonyl; by benzyl; by anilino; by monoalkylamino or dialkylamino, each with up to 4 carbon atoms in each alkyl moiety; or by a cyclic amine radical in which the amine nitrogen is a constituent of a 5-membered or 6-membered heterocyclic structure which can in addition contain at least one further hetero-atom selected from the group consisting of nitrogen, oxygen and sulfur ring members; it being possible for an aryl radical to be substituted by the group

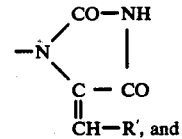

R' is hydrogen or alkyl with up to 6 carbon atoms, exhibit strong fungicidal properties.

11 Claims, No Drawings

COMBATING FUNGI WITH 1-ARYL-5-ALKYLIDENE-2,4-DIOXO-IMIDAZOLIDINES

The present invention relates to and has for its objects the combating of fungi with 1-aryl-5-aklylidene-2,4-dioxo-imidazolidines, and active compositions in the form of mixtures of such compounds with solid and liquid dispersible carrier vehicles, with other and further objects becoming apparent from a study of the within specification and accompanying examples.

The present invention relates to the use as fungicides of certain 1-aryl-5-alkylidene-2,4-dioxo-imidazolidines.

A fungicide which is well known for use in argiculture and horticulture is zinc ethylene-1,2-bis-dithiocarbamate (Compound A); this compound is of great importance among commercially available products (Compare R. Wegler, "Chemie der Pflanzenschutz-und Schadlingsbekampfungsmittel" ("Chemistry of Plant Protection Agents and Pesticides"), volume 2, page 65, Berlin/Heidelberg/New York (1970). However, the action is not always satisfactory at low use concentrations.

It has now been found that the 1-aryl-5-alkylidene-2,4-dioxo-imidazolidines of the formula

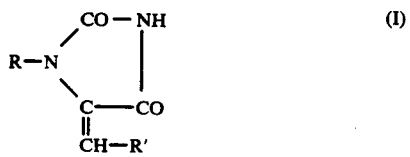

in which

R is aryl optionally substituted by nitro; by halogen; by alkyl, alkoxy, alkylthio, alkylsulfinyl or alkylsufonyl each with up to 6 carbon atoms; by haloalkyl with up to 5 halogen atoms and 1 or 2 carbon atoms; by cycloalkyl with 5 or 6 carbon atoms; by hydroxyl; by cyano; by thiocyanato; by acetyl; by formyl; by phenyl or phenoxy each optionally carrying halogen or nitro as substituents; by phenylthio; by phenylsulfonyl; by halosulfonyl; by benzyl; by anilino; by monoalkylamino or dialkylamino each with up to 4 carbon atoms in ech alkyl moiety; or by a cyclic amine radical in which the amine nitrogen is a constituent of a 5-membered or 6-membered heterocyclic structure which can in addition contain at least one further hetero-atom selected from the group consisting of nitrogen, oxygen and sulfur as ring members; it being possible for an aryl radical to be substituted by the group

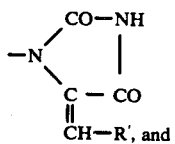

R' is hydrogen or alkyl with up to 6 carbon atoms, exhibit strong fungicidal properties.

Surprisingly, the 1-aryl-5-aklylidene-2,4-dioxoimidazolidines of the formula (I), to be used according to the invention, exhibit a better fungicidal action than the standard preparation mentioned at the outset. The use of active compounds according to the invention thus represents an enrichment of the art.

The following may be mentioned as examples of the compounds to be used according to the invention: 1-phenyl-5-methylene-2,4-dioxo-imidazolidine, 1-(3,4-dichloro-phenyl)-5-methylene-2,4-dioxo-imidazolidine, 1-(4-nitro-phenyl)-5-methylene-2,4-dioxo-imidazolidine, 1-(4-chloro-phenyl)-5-methylene-2,4-dioxo-imidazolidine, 1-(4-ethoxy-phenyl)-5-methylene-2,4-dioxo-imidazolidine, 1-naphthyl-(1)-5-methylene-2,4-dioxo-imidazolidine, 1-(2-chloro-phenyl)-5-methylene-2,4-dioxo-imidazolidine, 1-(4-bromo-phenyl)-5-methylene-2,4-dioxo-imidazolidine, 1-(4-iodo-phenyl)-5-methylene-2,4-dioxo-imidazolidine, 1-(3-nitro-phenyl)-5-methylene-2,4-dioxo-imidazolidine, 1-(2-nitro-phenyl)-5-methylene-2,4-dioxo-imidazolidine, 1-(3,5-dichloro-phenyl)-5-methylene-2,4-dioxo-imidazolidine, 1-(2,6-dichloro-phenyl)-5-methylene-2,4-dioxo-imidazolidine, 1-(4-hydroxy-phenyl)-5-methylene-2,4-dioxo-imidazolidine, 1-(3,5-dichloro-4-hydroxy-phenyl)-5-methylene-2,4-dioxo-imidazolidine, 1-(3,5-dichloro-4-cyano-phenyl)-5-methylene-2,4-dioxo-imidazolidine, 1-(3,5-dibromo-phenyl)-5-methylene-2,4-dioxo-imidazolidine, 1-(3,5-bis-trifluoromethylphenyl)-5-methylene-2,4-dioxo-imidazolidine, 1-(2,4,5-trichloro-phenyl)-5-methylene-2,4-dioxo-imidazolidine, 1-(4-chloro-3,5-dimethyl-phenyl)-5-methylene-2,4-dioxo-imidazolidine, 1-(4-dimethylamino-3-chloro-phenyl)-5-methylene-2,4-dioxo-imidazolidine, 1-(3,4-dimethoxy-phenyl)-5-methylene-2,4-dioxo-imidazolidine, 1-(4-chloro-2,5-diethoxy-phenyl)-5-methylene-2,4-dioxo-imidazolidine, 1-(2-chloro-5-formyl-phenyl)-5-methylene-2,4-dioxo-imidazolidine, 1-(4-phenoxy-phenyl)-5-methylene-2,4-dioxo-imidazolidine, 1-(3-chloro-4-(4'-chlorophenoxy)-phenyl)-5-methylene-2,4-dioxo-imidazolidine, 1-(3,5-dichloro-4-(4'-bromo-phenoxy)-phenyl)-5-methylene-2,4-dioxo-imidazolidine, 1-(3,5-dimethyl-4-(4'-chloro-phenoxy)-phenyl)-5-methylene-2,4-dioxo-imidazolidine, 1-(3-chloro-5-methyl-4-(2',4'-dichloro-phenoxy)-phenyl)-5-methylene-2,4-dioxo-imidazolidine, 1-(3,5-dibromo-4-(4'-nitro-phenoxy)-phenyl)-5-methylene-2,4-dioxo-imidazolidine, 1-(3-methyl-4-(4'-bromo-phenoxy)-phenyl)-5-methylene-2,4-dioxo-imidazolidine, 1-(3,5-dichloro-4-thiocyano-phenyl)-5-methylene-2,4-dioxo-imidazolidine, 1-(3,5-dichloro-4-ethylmercapto-phenyl)-5-methylene-2,4-dioxo-imidazolidine, 1-(2,4-dimethyl-phenyl)-5-methylene-2,4-dioxo-imidazolidine, 1-(2,6-diisopropyl-phenyl)-5-methylene-2,4-dioxo-imidazolidine, 1-(2-methyl-4-chloro-phenyl)-5-methylene-2,4-dioxo-imidazolidine, 1-(3,5-dichloro-4-(4'-iodophenoxy)-phenyl)-5-methylene-2,4-dioxo-imidazolidine, 1-(3,5-dichloro-4-(4'-chlorophenoxy-phenyl)-5-methylene-2,4-dioxo-imidazolidine, 1-(3-chloro-4-(4'-chloro-phenylsulfonyl)-phenyl)-5-methylene-2,4-dioxo-imidazolidine, 1-(1-chloronaphthyl-(2))-5-methylene-2,4-dioxo-imidazolidine, 1-(4-methoxy-naphthyl-(1))-5-methylene-2,4-dioxo-imidazolidine, 1-(3,4-dichloro-phenyl)-5-ethylidene-2,4-dioxo-imidazolidine, 1-(2,4-dichloro-phenyl)-5-ethylidene-2,4-dioxo-imidazolidine, 1-(4-chloro-2-methylphenyl)-5-ethylidene-2,4-dioxo-imidazolidine, 1-(3,5-dichloro-4-(4'-chloro-phenoxy)-phenyl)-5-ethylidene-2,4-dioxo-imidazolidene and 1-(3,5-dimethoxyphenyl)-5-ethylidene-2,4-dioxo-imidazolidine.

Particularly preferred compounds are those compounds of formula (I) in which R represents phenyl or naphthyl each of which optionally carries, as substituents, halogen (especially fluorine, chlorine or bromine), nitro, methyl, methoxy, ethyl, ethoxy, and/or the group

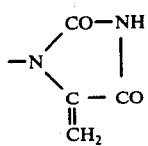

and R' represents hydrogen or methyl.

The compounds of the formula (I) were not previously known. They can be prepared by reacting N-aryl-N'-(2,3-dihalogeno-alkanoyl)-ureas with alkali metal alkoxides in the presence of a solvent at temperatures of 20° C to boiling point of the solvent, preferably 50° to 120° C.

The preferred alkali metal alkoxides are the sodium alkoxides or potassium alkoxides of lower alkanols as well as cycloalkanols, preferably potassium tert.-butylate.

Examples of possible solvents are alcohols and ethers; preferably, the alcohol which is used to prepare the alkali metal alkoxide is used as the solvent. Illustrative details are given in the Examples hereinbelow.

The N-aryl-N'-(2,3-dihalogeno-alkanoyl)-ureas required as intermediate products, as disclosed in application Ser. No 668,165, filed Mar. 18, 1976, may be obtained by reaction of 2,3-dihaloalkanoylisocyanates with primary arylamines in the presence of an inert solvent at a temperature of −20° to +50° C.

2,3-Dihaloalkanoyl-isocyanates, such as are employed as intermediate products for the process according to the invention, can be obtained by reaction of α,β-unsaturated carboxylic acid amides (such as acrylic acid amide or crotonic acid amide) with a halogen, preferably chlorine or bromine, to give 2,3-dihalo-carboxylic acid amides, followed by reaction of the latter with an excess of oxalyl chloride. This reaction can, if appropriate, be carried out without intermediate isolation of the 2,3-dihalo-carboxylic aced amides. The reactions may be carried out in the presence of a solvent, which may be a material inert towards isocyanates, preferably a halohydrocarbon, such as methylene chloride or chloroform.

The active compounds to be used according to the invention have a substantial fungitoxic activity and relatively low toxicity to warm-blooded animals, as a result of which they are relatively easy to handle and can be employed in practice to combat undesired fungal growth. Their good toleration by plants also permits their use against fungal plant diseases, by treating the standing crop plant or individual parts thereof, or the seed, or the soil in which the crop is grown.

Fungitoxic agents are employed in plant protection to combat fungi from the various categories thereof, for example Archimycetes, Phycomycetes, Ascomycetes, Basidiomycetes and Fungi Imperfecti.

The active compounds to be used according to the invention can be employed to combat fungi which attack the plant through the atmosphere or through the soil, and also to combat fungi which are transferred by plant seed. They are particularly active against the pathogens of bunt of wheat and against the pathogens of cereal rust.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such a gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphathlenes, etc.) halogenated, especially chlorinated, aromatic hydrocarbons (e.g. chlorobenzenes, etc.) cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sufates, akyll sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides or insecticides, acaricides, nematocides, bactericides, rodenticides, herbicides, fertilizers, growth-regulating agents, agents for improving the soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divider carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In the case of seed dressing, amounts of active compound of 10 mg to 10 g, preferably 100 mg to 3 g, are generally used per kilogram of seed. In the case of treatment of the soil, which can be carried out over the entire crop area, in strips or at back points, active compound concentrations of 1 to 1,000 g of active compound per m³ of soil, preferably 10 to 200 g per m³, are generally required at the location where the action is expected.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, slurry dressing, moist dressing, wet dressing, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Seed dressing test/bunt of wheat (seed-borne mycosis)

To produce a suitable dry dressing, the active compound was extended with a mixture of equal parts by weight of talc and kieselguhr to give a finely powdered mixture with the desired concentration of the active compound.

Wheat seed was contaminated with 5 g of the chlamydospores of *Tilletia caries* per kg of seed. To apply the dressing, the seed was shaken with the dressing in a closed glass flask. The seed, on moist loam under a cover of a layer of muslin and 2 cm of moderately moist compost soil, was exposed to optimum germination conditions for the spores for 10 days at 10° C in a refrigerator.

The germination of the spores on the wheat grains, each of which was contaminated with about 100,000 spores, was subsequently determined microscopically. The smaller the number of spores which had germinated, the more effective was the active compound.

The active compounds, the concentrations of the active compounds in the dressing, the amounts of dressing used and the percentage spore germination can be seen from the following table:

Table 1

| Active compounds | Seed dressing test/bunt of wheat | | |
| --- | --- | --- | --- |
| | Active compound concentration in the dressing in % by weight | Amount of dressing used in g/kg of seed | Spore germination in % |
| No dressing | — | — | >10 |
| 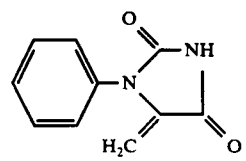 (known) (A) | 10 | 1 | 5 |
| (1) | 10<br>5 | 1<br>1 | 0.005<br>0.05 |

Table 1-continued

Seed dressing test/bunt of wheat

| Active compounds | Active compound concentration in the dressing in % by weight | Amount of dressing used in g/kg of seed | Spore germination in % |
|---|---|---|---|
| 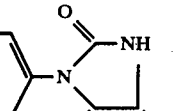 (3) | 10 | 1 | 0.5 |
| 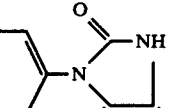 (4) | 10 | 1 | 0.5 |
| 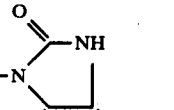 (6) | 10<br>5 | 1<br>1 | 0.05<br>0.5 |
| 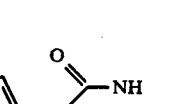 (5) | 10<br>5 | 1<br>1 | 0.005<br>0.05 |

EXAMPLE 2

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C and 100% relative atmospheric humidity.

After 10 days dwell time of the plants at a temperature of 20° C and 80–90% atmospheric humidity, the occurrence of rust pustules on the plant was evaluated. The degree of infection is expressed as a percentage of the infection of the untreated control plants. 0% denotes no infection and 100% denotes the same degree of infection as in the case of the untreated control. The active compound is the more active, the lower is the degree of rust infection.

The active compounds, active compound concentrations in the spray liquor and degrees of infection can be seen from the table which follows:

Table 2

Shoot treatment test/cereal rust/protective

| Active compounds weight | Active compound concentration in the spray liquor in % by weight | Infection in % of the untreated control |
|---|---|---|
| Untreated | — | 100 |
| CH$_2$—NH—CS—S\\<br>                      Zn<br>CH$_2$—NH—CS—S/<br>(A) | 0.025 | 93.8 |

Table 2-continued

Shoot treatment test/cereal rust/protective

| Active compounds weight | Active compound concentration in the spray liquor in % by weight | Infection in % of the untreated control |
|---|---|---|
| (1) Phenyl-N, H₂C=C(O), C(=O)-NH hydantoin-like structure | 0.025 | 32.5 |
| (4) 4-O₂N-phenyl analog | 0.025 | 0.0 |
| (5) 4-Cl-phenyl analog | 0.025 | 32.5 |
| (6) 1-naphthyl analog | 0.025 | 32.5 |

EXAMPLE 3

Mycelium growth test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture
0.19 part by weight of DMF or acetone
0.01 part by weight of emulsifier (alkylaryl polyglycol ether)
1.80 parts by weight of water
2 parts by weight of solvent mixture
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent. The concentrate was thoroughly mixed, in the stated proportion, with the liquid nutrient medium (which had been cooled to 42° C) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evalutation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:
1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

Table 3

| Active compound | Active compound concentration, ppm | Mycelium growth test — Fungi | | | | | | |
|---|---|---|---|---|---|---|---|---|
| | | Verti-cillium alboatrum | pyricu-laria oryzae | Helmintho-sporium gramineum | Mycos-phorella musicola | Phyto-phthora cactorum | Venturia inaequalis | Pellicul-aria sasakii |
| 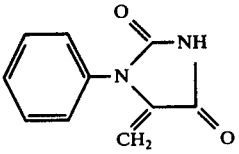 (known) (A) | 10 | 9 | 9 | 5 | 5 | 9 | 9 | 9 |
| 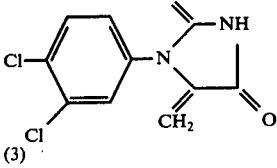 (1) | | 5 | 1 | 3 | 1 | 1 | 1 | 3 |
| 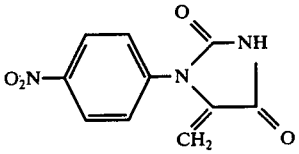 (3) | | 5 | 1 | 1 | 1 | 2 | 1 | 3 |
| 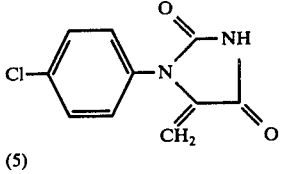 (4) | 10 | −1 | 3 | 5 | 3 | 1 | 5 | |
| 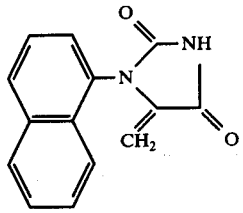 (5) | | 5 | 1 | 3 | 1 | 1 | 1 | 1 |
| (6) | | 5 | 1 | 3 | — | 3 | 3 | 5 |

The following further examples are set forth to illustrate, without limitation, the manner of producing the instant compounds according to the present invention:

EXAMPLE 4 a. Starting material: 2,3-dibromopropionyl-isocyanate.

100 g (1.41 moles) of acrylic acid amide were dissolved in 1,200 ml of chloroform and 224 g (1.41 moles) of bromine, dissolved in 250 ml of chloroform, were added dropwise to the solution at a temperature of 0° to 5° C, while stirring. The resulting suspension was stirred for a further 5 hours at 20° C. 270 g (2.13 moles) of oxalyl chloride were then added dropwise, with continued stirring, and thereafter the reaction mixture was heated to the boil and was kept at the boil, under reflux, until the evolution of gas had ceased. The reaction mixture was then subjected to fractional distillation; this gave 220 g (61% of theory) of 2,3-dibromopropionyl-isocyanate of boiling point 73° to 75° C/2.5 mm Hg.

b. Intermediate product: N-phenyl-N'-(2,3-dibromopropionyl)urea.

9.5 g of aniline were dissolved in 100 ml of anhydrous benzene and a solution of 26.0 g of 2,3-dibromopropionylisocyanate in 100 ml of benzene was added dropwise at 10° to 15° C, while cooling. The mixture was stirred for a further 2 hours, the crystal paste was diluted with an equal volume of petroleum ether and the product was filtered off, washed with petroleum ether and dried. 30 g of the desired compound were obtained; the melting point was about 160°–161° C.

c) 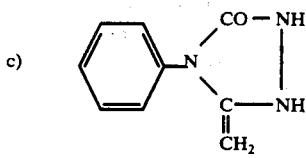 (1)

20.0 g (0.057 mole) of N-phenyl-N'-(2,3-dibromopropionyl)-urea were suspended in 200 ml of tert.-butanol, 23 g of potassium tert.-butylate (90% strength, approximately 0.2 mole) were introduced and the mixture was then heated under reflux for 1 hour. Thereafter the solvent was distilled off under normal pressure and the residue was warmed to 120° C in vacuo for 20 minutes. The resulting colorless crystalline powder was dissolved in 400 ml of water at 60° C and the solution was filtered and brought to pH 1 with dilute hydrochloric acid. The imidazolidine derivative which had precipitated was filtered off, washed and dried. 9 g of 1-phenyl-5-methylene-2,4-dioxo-imidazolidine of melting point 168°-170° C (recrystallized from methanol) were obtained. The yield was 84% of theory.

EXAMPLE 5 a. Intermediate product: N-(4-ethoxyphenyl)-N'-(2,3-dibromopropionyl)-urea 30.0 g of 4-ethoxy-aniline were dissolved in 400 ml of dry benzene and a solution of 57.0 g of 2,3-dibromopropionylisocyanate in 200 ml of benzene was added dropwise at 0° to 5° C while cooling. After completion of the reaction, the suspension produced was diluted with an equal volume of petroleum ether and the reaction product was filtered off and dried. 72 g of the desired product were obtained. The melting point was 172°-174° C.

b) 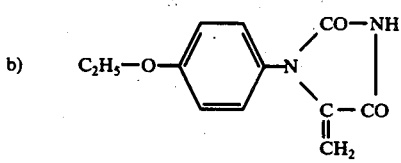 (2)

70 g (0.178 mole) of N-(4-ethoxyphenyl)-N'-(2,3-dibromopropionyl)-urea and 72 g of potassium tert.-butylate (90% strength, about 0.58 mole) in 400 ml of tert.-butanol were heated under reflux for 30 minutes, the solvent was distilled off and the residue was warmed to 120° C in vacuo for 20 minutes. The batch was then taken up in 500 ml of hot water, the mixture was filtered and the filtrate was acidified with dilute hydrochloric acid. The product which had precipitated was filtered off and dried. 30 g of 1-(4-ethoxyphenyl)-5-methylene-2,4-dioxo-imidazolidine were obtained.

| Analysis: | $C_{12}H_{12}N_2O_3$; | | molecular weight 232.24 | |
|---|---|---|---|---|
| Calculated | C 62.06 | H 5.21 | N 12.07 | O 20.67 |
| Found | C 61.8 | H 5.3 | N 12.2 | O 20.5 |
| | C 62.1 | H 5.4 | N 12.3 | O 20.8 |

The following compounds of the general formula

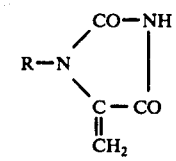

were prepared analogously:

Table 4

| Compound No. | R | Melting point (° C) |
|---|---|---|
| 3 | Cl-(2,4-dichlorophenyl)- | 234–236 |
| 4 | $O_2N$-(4-nitrophenyl)- | 201–202 (with decomposition) |
| 5 | Cl-(4-chlorophenyl)- | 185–187 |
| 6 | naphthyl | 193–195 |
| 7 | NH—CO, CO—C(=CH₂)—N-phenyl- | 340 (with decomposition) |
| 8 | 2,3-dichlorophenyl | 201–203 |
| 9 | Cl-, CH₃-phenyl | 123–125 |
| 10 | CH₃-, CH₃-phenyl | 163–165 |

It will be appreciated that the instant specification and examples are set forth by way of illustration and not limitation, and that various modifications and changes may be made without departing from the spirit and scope of the present invention.

What we claim is:

1. A method of combating fungus pests which comprises applying to the pests or a habitat thereof a fungicidally effective amount of a compound of the formula

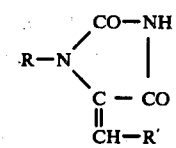

in which

R is phenyl or naphthyl; or phenyl or naphthyl substituted by nitro; by halogen; by alkyl, alkoxy, alkylthio, alkylsulfinyl or alkylsulfonyl each with up to 6 carbon atoms; by haloalkyl with up to 5 halogen atoms and 1 or 2 carbon atoms; by cycloalkyl with 5 or 6 carbon atoms; by hydroxyl; by cyano; by thiocyanato; by acetyl; by formyl; by phenyl or phenoxy each optionally carrying halogen or nitro as substituents; by phenylthio; by phenylsulfonyl; by halosulfonyl; by benzyl; by anilino; by monoalkylamino or dialkylamino, each with up to 4 carbon atoms in each alkyl moiety; or by

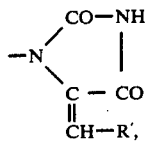

and R' is hydrogen or alkyl with up to 6 carbon atoms.

2. The method according to claim 1, in which R is phenyl or naphthyl optionally substituted by at least one member selected from the group consisting of fluorine, clorine, bromine, nitro, methyl, methoxy, ethyl, ethoxy and the group

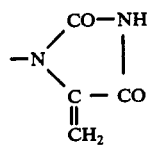

and R' is hydrogen or methyl.

3. The method according to claim 1 in which the active compound is applied to seed as dressing in an amount of about 10 mg to 10 g per kilogram of seed.

4. The method according to claim 1 in which the active compound is applied to soil of a crop area in an amount of about 1 to 1000 g per m³ of soil.

5. The method according to claim 1, in which the active compound is 1-phenyl-5-methylene-2,4-dioxo-imidazolidine of the formula

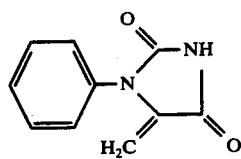

(1)

6. The method according to claim 1, in which the active compound is 1-(3,4-dichlorophenyl)-5-methylene-2,4-dioxo-imidazolidine of the formula

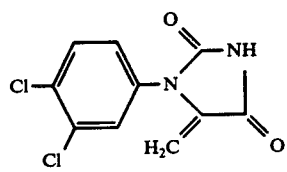

(3)

7. The method according to claim 1, in which the active compound is 1-(4-nitrophenyl)-5-methylene-2,4-dioxo-imidazolidine of the formula

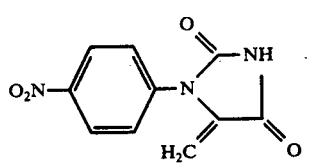

(4)

8. The method according to claim 1, in which the active compound is 1-(4-chlorophenyl)-5-methylene-2,4-dioxo-imidazolidine of the formula

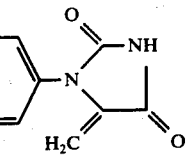

(5)

9. The method according to claim 1, in which the active compound is 1-(naphthyl-(1))-5-methylene-2,4-dioxo-imidazolidine of the formula

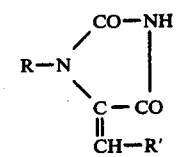

(6)

10. A fungicidal composition comprising a diluent and a fungicidally effective amount of 1-aryl-5-alkylidene-2,4-dioxo-imidazolidine of the formula

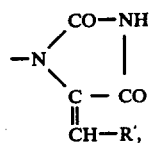

in which
R is phenyl or naphthyl; or phenyl or naphthyl substituted by nitro; by halogen; by alkyl, alkoxy, alkylthio, alkylsulfinyl or alkylsulfonyl each with up to 6 carbon atoms; by haloalkyl with up to 5 halogen atoms and 1 or 2 carbon atoms; by cycloalkyl with 5 or 6 carbon atoms; by hydroxyl, by cyano; by thiocyanato; by acetyl; by formyl; by phenyl or phenoxy each optionally carrying halogen or nitro as substituents; by phenylthio; by phenylsulfonyl; by halosulfonyl; by benzyl; by anilino; by monoalkylamino or dialkylamino, each with up to 4 carbon atoms in each alkyl moiety; or by

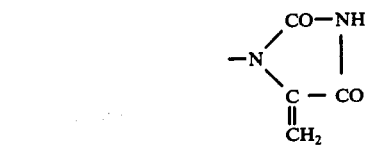

and R' is hydrogen or alkyl with up to 6 carbon atoms.

11. The composition according to claim 1 in which the active compound is a member selected from the group consisting of 1-phenyl-5-methylene-2,4-dioxo-imidazolidine, 1-(3,4-dichlorophenyl)-5-methylene-2,4-dioxo-imidazolidine, 1-(4-nitrophenyl)-5-methylene-2,4-dioxo-imidazolidine, 1-(4-chlorophenyl)-5-methylene-2,4-dioxo-imidazolidine and 1-(naphthyl-(1))-5-methylene-2,4-dioxo-imidazolidine.

* * * * *